United States Patent [19]

Narciso, Jr.

[11] Patent Number: 5,298,018

[45] Date of Patent: Mar. 29, 1994

[54] METHOD FOR TREATING CARDIOVASCULAR DISEASE THROUGH ADJUNCTIVE PHOTODYNAMIC THERAPY

[75] Inventor: Hugh L. Narciso, Jr., Santa Barbara, Calif.

[73] Assignee: PDT Cardiovascular, Inc., Goleta, Calif.

[21] Appl. No.: 930,860

[22] Filed: Aug. 14, 1992

[51] Int. Cl.$^5$ .............................................. A61N 1/30
[52] U.S. Cl. ..................................... 604/21; 128/898; 606/2; 606/15; 604/19
[58] Field of Search ................................... 604/19–22, 604/96; 128/898; 606/194, 2, 7, 192, 8, 15; 623/1, 11, 12

[56] References Cited

U.S. PATENT DOCUMENTS

| | | |
|---|---|---|
| 4,512,762 | 4/1985 | Spears . |
| 4,773,899 | 9/1988 | Spears .................................. 604/20 |
| 4,886,831 | 12/1989 | Morcos et al. ........................ 604/21 |
| 4,932,934 | 6/1990 | Dougherty et al. . |
| 5,015,463 | 5/1991 | Dougherty et al. . |
| 5,116,864 | 5/1992 | March et al. ......................... 514/455 |
| 5,169,395 | 12/1992 | Narciso, Jr. . |
| 5,179,120 | 1/1993 | Vogel et al. .......................... 604/20 |
| 5,199,951 | 4/1993 | Spears .................................. 604/96 |

OTHER PUBLICATIONS

Dartsch et al., "Growth Characteristics and Cytoskeletal Organization of Cultured Smooth Muscle Cells from Human Primary Stenosing and Restenosing Lesions", *Arteriosclerosis* 10(1):62–75 (1990).

Dartsch et al., "Responses of Cultured Smooth Muscle Cells from Human Nonatherosclerotic Arteries and Primary Stenosing Lesions After Photoradiation: Implications for Photodynamic Therapy of Vascular Stenoses", *JACC* 15(7):1545–1550 (1990).

Spokojny et al., "Uptake of Hematoporphyrin Derivative by Atheromatous Plaques; Studies in Human in Vitro and Rabbit in Vivo", *JACC* 8(6):1387–1392 (1986).

Delettre et al., "In vitro Uptake Of Dicarboxylic Porphyrins By Human Atheroma, Kinetic and Analytical Studies", *Photochemistry and Photobiology* 54(2):239–246 (1991).

Dartsch et al., "A comparison of dipyridamole and beta carotene with doxycycline for photodynamic reactions in vitro: results from human cell culture studies", *Coronary Artery Disease* 1(2):251–255 (1990).

Morgan et al., "Tin (IV) Etiopurpurin dichloride: An alternative to DHE?", *New Direction in Photodynamic Therapy* 847:172–179 (1987).

Dartsch et al, "Photodynamic Therapy of Vascular Stenoses?" *Photodynamic Therapy* III-10:77–80.

Merck Index (10th edition) pp. 559 & 670 (1983).

*Primary Examiner*—C. Fred Rosenbaum
*Assistant Examiner*—Chalin Smith
*Attorney, Agent, or Firm*—Townsend and Townsend Khourie and Crew

[57] ABSTRACT

Photodynamic Therapy (PDT) is used as an adjunctive or stand alone procedure for the treatment of cardiovascular disease. When used as an adjunctive therapy to Percutaneous Transluminal Coronary Angioplasty, laser angioplasty, atherectomy, stenting, or any other interventional or surgical procedure, it has been found that the treatment timing is critical to the success of the combined therapies. A photosensitizer is administered prior to the surgical or interventional procedure and then readministered after the procedure to maintain the photosensitizer concentration level in the atheromatous plaque and smooth muscle cells in the vicinity of the lesion for a period of about 5–18 days, the period in which cell proliferation can occur. The photosensitizer inhibits smooth muscle cell proliferation and, thus, minimizes or eliminates the possibility of re-stenosis. The photosensitizer is then illuminated at the end of this period, thereby lysing the atheromatous plaque and smooth muscles. The photosensitizer inhibits atheromatic smooth muscle cell proliferation.

14 Claims, 4 Drawing Sheets

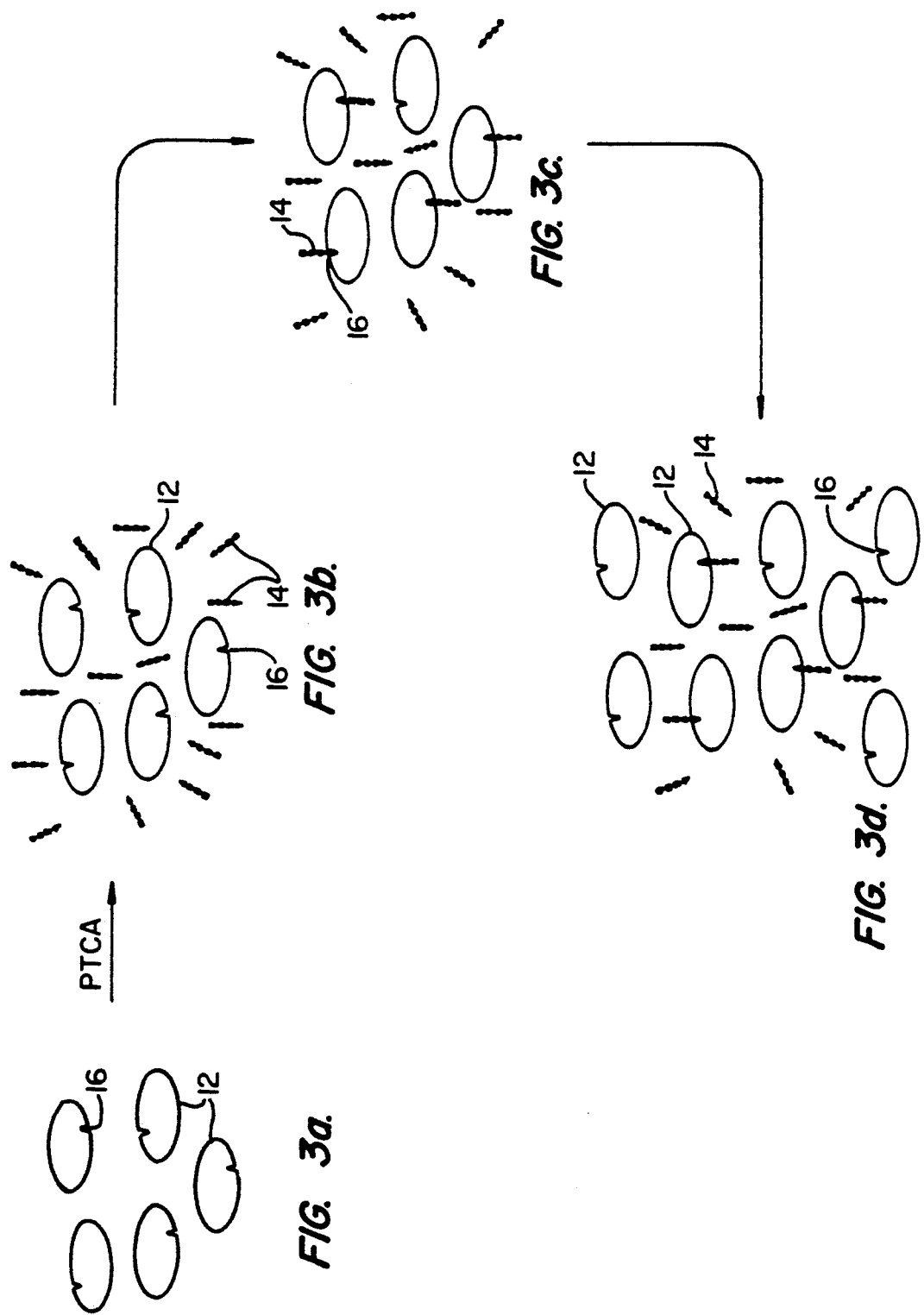

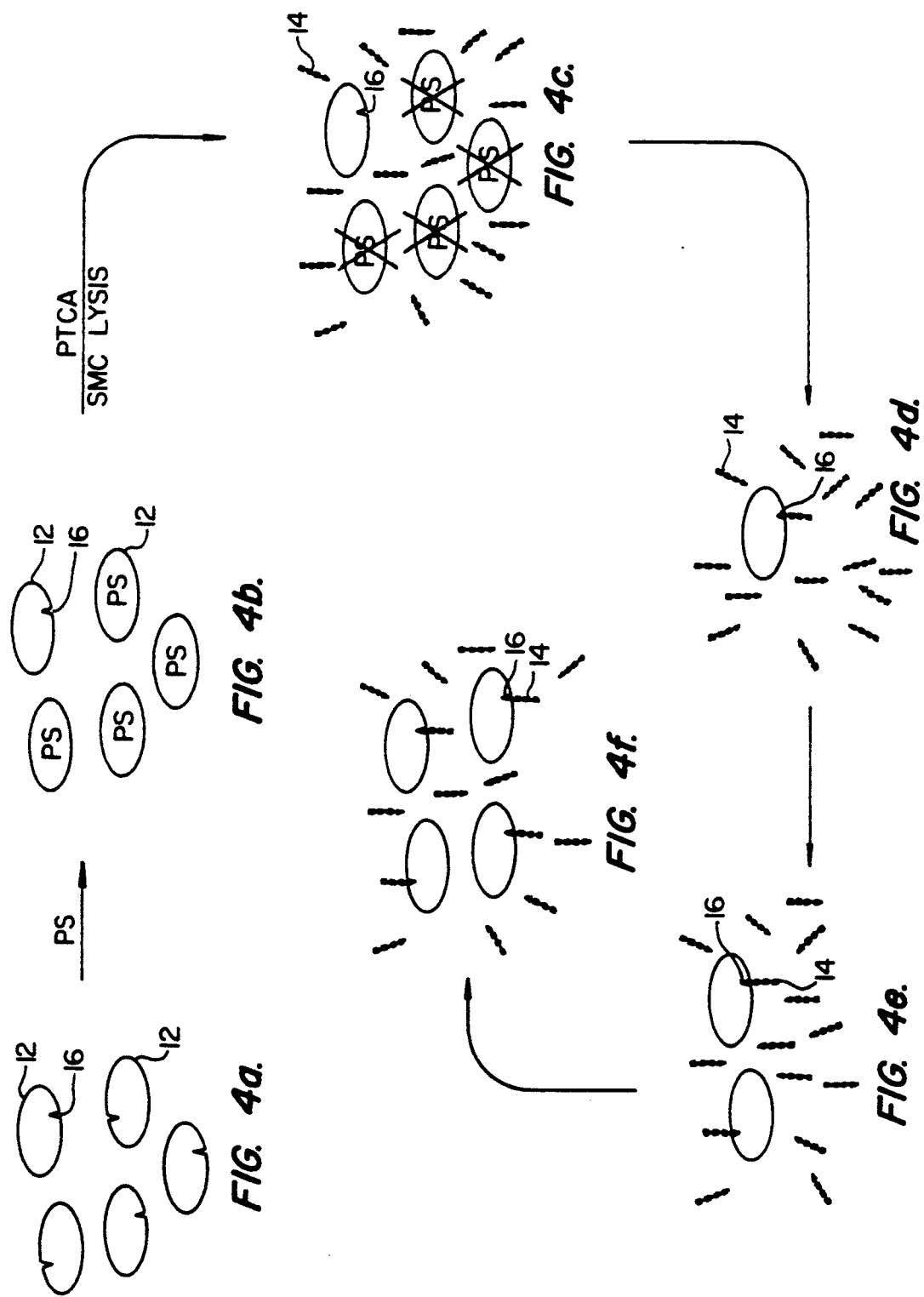

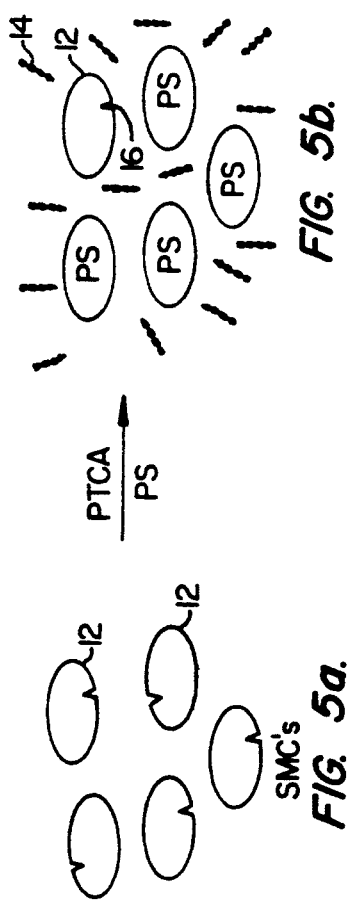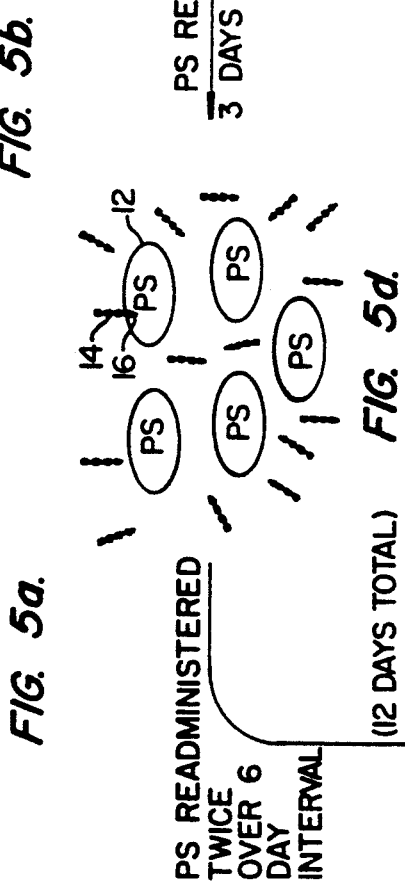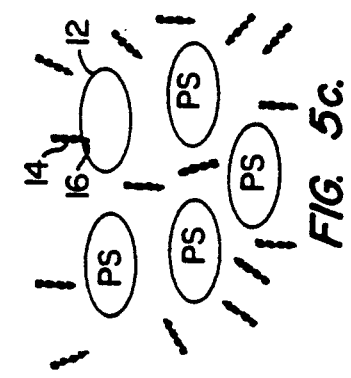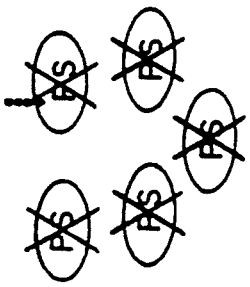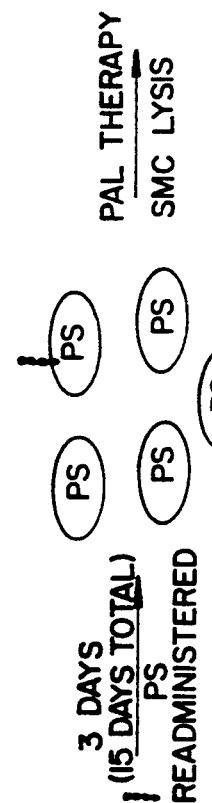

METHOD FOR TREATING CARDIOVASCULAR DISEASE THROUGH ADJUNCTIVE PHOTODYNAMIC THERAPY

BACKGROUND OF THE INVENTION

The present invention relates to treatment of cardiovascular disease generally, and more particularly to treatment of atherosclerosis through adjunctive photodynamic therapy.

Atherosclerosis is a cardiovascular disease in which deposits of plaques (atheromas) containing cholesterol, lipid material, foam cells, lipophages, and proliferating smooth muscle cells are within the intima and media of large to small diameter arteries such as the aorta and the iliac, femoral, coronary, and cerebral arteries. The resultant stenosis causes reduction in blood flow.

Attempts to treat atherosclerosis have included bypass surgery wherein the diseased vascular segments are augmented by prosthetic or natural grafts. This procedure requires general anesthesia and a substantial healing period after surgery and, thus, is generally limited to cases of severe coronary artery disease.

Other approaches for primary treatment of stenotic vessels include percutaneous transluminal coronary angioplasty (PTCA), atherectomy, stenting and newer modalities of cardiovascular intervention including laser angioplasty. The primary drawbacks of these methods has been re-stenosis. Studies have shown that re-stenosis, or the re-narrowing of the internal lumen of an artery, subsequent to such primary treatment occurs in about 25-50% of cases where such primary treatment is performed. The result of re-stenosis is the requirement for an additional interventional or surgical procedure.

Various mechanisms can cause re-stenosis. One mechanism is rapid smooth muscle cell (SMC) proliferation at the lesion site. Smooth muscle cell proliferation is believed to occur immediately or at any time up to several hours after vessel wall injury that results from primary atherosclerotic treatment such as angioplasty. This proliferation continues for about 5-18 days depending on the individual. The cause of this rapid smooth muscle cell proliferation is believed to involve the release of various growth factors in response to the vessel wall injury. Specifically, after such vessel wall injury, some smooth muscle cells migrate to the intima where they are affected by the blood elements with which they come in contact, especially platelets and lipoproteins. Platelets contain a factor that stimulates smooth muscle cell proliferation and migration, which can result in re-stenosis.

Accordingly, there is a need to address the problem of smooth muscle cell proliferation in the treatment of atherosclerosis to minimize or eliminate the occurrence of re-stenosis.

SUMMARY OF THE INVENTION

The present invention is directed to a method for treating vascular disease that avoids the problems and disadvantages of the prior art. The invention accomplishes this goal by providing a method for treatment of atherosclerosis comprising the steps of widening the lumen of a vessel that has narrowed due to accumulation of atheromatous plaque (e.g., by angioplasty or atherectomy), and blocking the growth factor binding sites on the atherosclerotic smooth muscle cells (SMC) injured during the widening step until growth factor is no longer released from the platelets in the vicinity of the injured cells. In this way, smooth muscle cell proliferation in the vicinity of the lesion site is inhibited, thereby minimizing or eliminating the occurrence of re-stenosis.

In the preferred embodiment, the blocking step is accomplished by introducing a photosensitizing agent in the region of the vessel subject to the widening step such that the agent accumulates in the atheromatous plaque and injured smooth muscle cells. The photosensitizer, accumulated in the atheromatous plaque and smooth muscle cells, blocks the smooth muscle cell growth factor binding sites to inhibit smooth muscle cell proliferation and, therefore, preferably is intravenously administered before the vessel lumen widening procedure to ensure its presence before growth factor release. Alternatively, the photosensitizer can be administered after angioplasty or atherectomy procedures. However, in the latter case, it should be administered immediately after such procedures (i.e., within about two hours of such procedures) to prevent growth factor from stimulating smooth muscle cell proliferation. In either case, the photosensitizer is readministered after angioplasty or atherectomy for a period of about 5-18 days, which corresponds to the period needed for growth factor release from platelets to terminate and which varies among patients. The continued readministration of photosensitizer serves to replace previously administered photosensitizer, which is cleared from the cells over time, to ensure that the growth factor binding sites are blocked until growth factor has cleared from the tissues. After the last administration of the photosensitizing agent and before it clears from the atherosclerotic smooth muscle cells and plaque, the photosensitizing agent is exposed to light at a wavelength at which the photosensitizer absorbs the light causing cell lysis. Since the growth factor has cleared before atherosclerotic plaque and cell lysis, the likelihood of re-stenosis is significantly reduced or eliminated. The process of activating a photosensitizer with light to cause cell necrosis is called photodynamic therapy, or more particularly in the case of atherosclerosis, photoatherolytic therapy.

The preferred photosensitizing agent is Tin Ethyl Etiopurpurin. It has been found that there is little or no retention of this drug in the skin, thereby avoiding problems that can result from exposure of the patient to ordinary sunlight (i.e., activation of the photosensitizer in the skin). In addition, Tin Ethyl Etiopurpurin has a high therapeutic ratio (concentration level in diseased tissue relative to healthy tissue) as compared to other photosensitizers such as hematoporphyrin derivative (HPD). Tin Ethyl Etiopurpurin also is advantageously activated at longer wavelengths (660-690 nanometers). At these wavelengths, the light is significantly less attenuated by the blood as is the case with 630 nanometer wavelength light (the optimum wavelength for HPD, for example). As a result of using a longer activation wavelength, a substantially greater amount of light gets to the vessel wall and photosensitizer, thereby increasing procedure efficiencies.

In summary, the above treatment has the potential to greatly impact the treatment of cardiovascular disease by treating the disease from a cellular cause level (the atherogenesis perspective) and not merely from the conventional palliative approach.

Although the most important application of this novel method is to improve the effectiveness of angioplasty or atherectomy of coronary arteries, this technique also can be applied to atherosclerotic arteries located elsewhere, such as the renal, iliac, femoral and popliteal arteries. Additionally, this technique can be used to prevent arterial occlusion after coronary bypass surgery wherein vascular segments are replaced with prosthetic or natural grafts and growth factor is released in response to the arterial wall injury.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIGS. 3a-d are a diagrammatic representation of smooth muscle cell proliferation following cardiovascular intervention;

FIG. 4 is a diagrammatic representation of concurrent cardiovascular intervention and photodynamic therapy involving a single administration of photosensitizer; and FIG. 5 is a diagrammatic representation of cardiovascular intervention and adjunct photodynamic therapy involving repeated administration of photosensitizer according to the principles of the present invention.

DESCRIPTION OF THE PREFERRED EMBODIMENT

Figure 1:
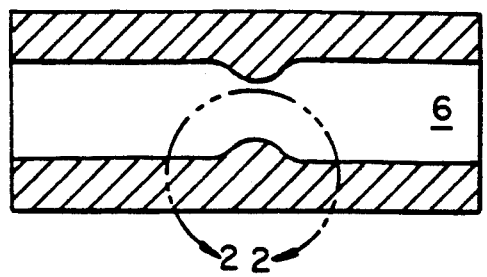
FIG. 1 is a longitudinal sectional view of an atherosclerotic artery.
Figure 2:
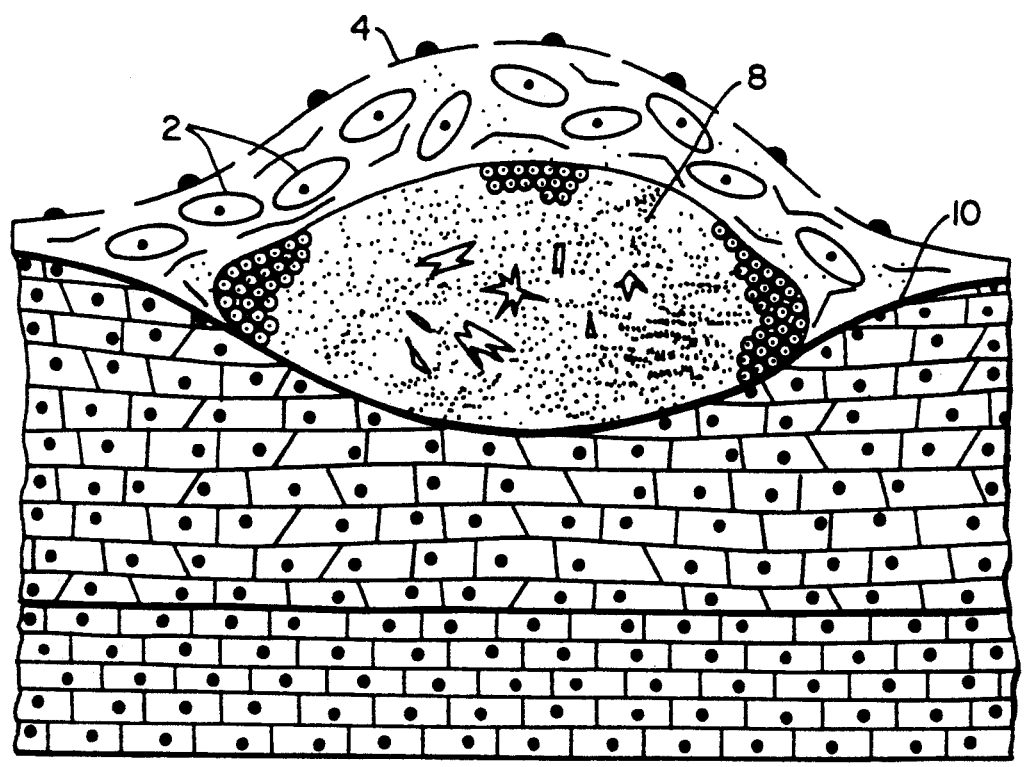
FIG. 2 is an enlarged view of the arterial wall of FIG. 1 taken along line 2—2.

To fully appreciate the treatment of atherosclerosis in accordance with the principles of the present invention, one must first understand the process of atherogenesis. Referring to FIGS. 1 and 2, atherogenesis, or the creation and proliferation of atherosclerosis, is characterized by a proliferation of smooth muscle cells (SMC) in the media of the vessel wall and beneath the intima 4. Over time this proliferation causes a reduction in the caliber of the arterial lumen 6 and the aggregation of dead smooth muscle cells, cholesterol, calcium, foam cells, macrophages, and phagocytes that form atherosclerotic plaque 8. This is the primary stenosing mechanism.

Subsequent to percutaneous transluminal coronary angioplasty, atherectomy or laser angioplasty to remove the stenosis, gross damage is done to the intimal surface of the vessel as the attempt is made to remove the calcium, cholesterol, etc. from the diseased vessel. In response to this gross damage, the human immune system initiates a second and distinct proliferation of smooth muscle cells to effect repairs on the intimal surface.

Generally, when the internal elastic lamina 10 is ruptured, smooth muscle cells therebelow migrate into the intima 4. These cells, which migrate into the intima are exposed to growth factors, such as platelet-derived growth factor which is released from the platelets that deposit themselves on these smooth muscle cells at the site of injury. This results in smooth muscle cell proliferation and re-stenosis.

The above mechanism is diagrammatically illustrated in FIGS. 3a-d where smooth muscle cells are designated with reference numeral 12. Taking coronary balloon angioplasty as an example of cardiovascular intervention, an inflatable balloon is inserted in a coronary artery at the region of a coronary narrowing. Following balloon inflation to widen the lumen of the artery, disruption of the arterial wall and atheromatous plaque occurs, including fracture of the plaque, rupture of the internal elastic lamina and separation of tissue layers. Platelets and microthrombi in the blood stream accumulate on the injured smooth muscle cells that migrate into the intima as a result of the vessel wall injury. Those platelets and microthrombi release growth factor, which is designated in FIG. 3b with reference numeral 14. The growth factor binds to the smooth muscle cells at smooth muscle cell binding sites 16 (FIG. 3c), which results in smooth muscle cell proliferation (FIG. 3d). This mechanism contributes to the greater than 25% incidence of re-stenosis within three to six months (the standard following period for interventional therapies) following successful percutaneous transluminal coronary angioplasty.

According to the present invention, photodynamic therapy is used as an adjunctive procedure to primary atherosclerotic treatment, such as percutaneous transluminal coronary angioplasty, laser angioplasty, and atherectomy to minimize or eliminate the occurrence of re-stenosis. Photodynamic therapy is more appropriately called photoatherolytic therapy (light induced atheromatous SMC lysis) in the specific case of cardiovascular disease.

Photodynamic therapy involves the administration of a pharmaceutical called a photosensitizer, preferably by intravenous injection into an atherosclerotic patient. The photosensitizer, when administered intravenously, is selectively retained by the atheromatous smooth muscle cells and plaque, with little or no retention into healthy areas of the arterial wall. Generally, the photosensitizer is nontoxic to all cells when administered, but once activated by a therapeutic dose of light commonly delivered by a laser at a specific wavelength, the photosensitizer, which has been selectively absorbed in the atherosclerotic cells, becomes toxic. In this way, the activated photosensitizer facilitates the destruction and reabsorption of the host atheromatous plaque and smooth muscle cells (cell necrosis). The mechanism of cell necrosis induced by photodynamic therapy is believed to involve a photochemical reaction that produces a species of oxygen called singlet oxygen, which induces cell death.

Since the surrounding healthy tissue does not retain the photosensitizer to the extent the diseased tissue does, the therapeutic dose of light is benign to the healthy tissue regions resulting in selective necrosis. This process is disclosed using Hematoporphyrin Derivative (HPD) as the photosensitizer in U.S. Pat. No. 4,512,762 to Spears, the disclosure of which is hereby incorporated herein by reference.

According to the present invention, the photosensitizer is administered in such a way to inhibit smooth muscle cell proliferation in addition to facilitating photodynamic therapy. It has been found that photosensitizers that have accumulated in smooth muscle cells act as a competitive inhibitor to block the growth factor binding site, thus preventing the smooth muscle cells from getting "switched on" by growth factor, which would otherwise cause rapid cell proliferation. However, since proliferation of smooth muscle cells occurs immediately or at any time up to several hours after vessel wall injury and continues for about 5 to 18 days (depending on the individual), the timing of the administration of the photosensitizer is critical to the present invention. The effect of the timing of the photosensitizer administration is discussed in detail below.

Referring to FIGS. 4a–f, cardiovascular interventional treatment accompanied by photodynamic therapy using a single administration of photosensitizer is diagrammatically shown, wherein smooth muscle cell proliferation results. Specifically, the photosensitizer is administered 24–48 hours before the combined primary treatment (e.g., angioplasty) and photodynamic destruction of the atherosclerotic smooth muscle cells and plaque that retain the photosensitizer. However, the administration of the photosensitizer does not necessarily result in accumulation of the drug in all of the atherosclerotic smooth muscle cells as illustrated in FIG. 4b where the cells that have absorbed photosensitizer are designated with the reference character PS. Factors such as biological variability and smooth muscle cell position (e.g., underlying cells being shielded by overlying cells) can influence whether photosensitizer is absorbed. FIG. 4b illustrates a 20% nonabsorption rate, i.e., four of five cells absorb the photosensitizer. Accordingly, when the smooth muscle cells are subjected to light at the appropriate wavelength, 80% of these cells are lysed (FIG. 4c). The remaining cell (which represents 20% of the cell group without photosensitizer) is exposed to growth factor.

As discussed above, growth factor is released in response to arterial wall injury as a result of the primary treatment (e.g., angioplasty). Since release of growth factor continues for about 5–18 days after arterial wall injury, the ubiquitous growth factors are free to "switch on" the remaining smooth muscle cells, resulting in rapid smooth muscle cell proliferation (FIGS. 4d–f) and re-stenosis. Thus, although concurrent or sequential treatment of atheroma with coronary angioplasty (or other interventional therapy) and photodynamic therapy (using a single administration of photosensitizer) reduces the initial proliferation of smooth muscle cells, in the long term such treatment may not be effective.

The preferred method of administering photosensitizer and providing adjunct therapy to cardiovascular intervention is diagrammatically illustrated in FIGS. 5a–g, where a photosensitizer having a three day smooth muscle cell clearance rate is used for purposes of example. The method involves blocking the smooth muscle cell growth factor binding sites to prevent smooth muscle cell proliferation throughout the growth factor release period. Generally, the photosensitizer is administered before cardiovascular interventional treatment, and then readministered at intervals corresponding to the time it takes the drug to clear from the cells.

Readministration is repeated until growth factor is no longer present (i.e., until the active component of the platelets that have accumulated on injured cells are exhausted such that growth factor is no longer released). The period it takes for an effective amount of the drug to clear from the plaque and atherosclerotic cells varies depending on the selected photosensitizer. For example, HPD clears from the cells in about three days and, thus, requires readministration before the expiration of each three-day period to ensure that the smooth muscle cell binding sites remain blocked until growth factor is no longer released. It should be understood that although all of the HPD may not clear the atheromatous plaque and smooth muscle cells after three days, the level of concentration of the drug in those cells after three days would fall below a level that would provide an effective amount of the drug for smooth muscle cell proliferation inhibition and cell lysis.

As in the previous case, not all of the cells absorb the drug after the initial administration. A 20% nonabsorption rate is illustrated in FIG. 5b as an example but will vary patient to patient. As shown in FIG. 5b, one of five cells is represented without photosensitizer and, thus, with its binding site exposed to growth factor (released after interventional treatment) which binds to the cell as illustrated in FIG. 5c.

When a photosensitizer having a three-day smooth muscle cell clearance rate is used, the drug is readministered before the expiration of three days from the initial administration. This results in about a 99% absorption rate with photosensitizer essentially absorbed in all of the smooth muscle cells likely to proliferate, as shown in FIG. 5d. The time that the growth factor is bound to the smooth muscle cell before readministration of the drug (i.e., a maximum of three days) is insufficient to cause cell proliferation. In addition, once the readministered photosensitizer is absorbed by the cell, previously without the drug and having growth factor attached to it, the absorbed photosensitizer renders the attached growth factor ineffective and prevents cell proliferation. Since the photosensitizer has a three day clearance rate, it is readministered at three-day intervals as the growth factor clears from the tissues (FIGS. 5e–f). After the last administration of the photosensitizer and before it clears from the atherosclerotic smooth muscle cells and plaque, the photosensitizer is exposed to light at a wavelength where the photosensitizer absorbs light, and cell lyses results, as illustrated in FIG. 5g. Since the growth factor has cleared before atherosclerotic plaque and cell lysis, the likelihood of re-stenosis is significantly reduced or eliminated.

The apparatus for irradiating the atherosclerotic tissue is conventional and generally includes a light source, which can be a laser system, a fiber optic delivery system positioned to radiate a lesion, and a radiation monitor and control system interfaced between the light source and delivery system as is conventional in the art and disclosed in U.S. Pat. No. 5,028,621 to Dougherty et al (hereby incorporated herein by reference).

In a preferred technique, the patient is catheterized with a light-emitting catheter inserted into the diseased vessel so that the light-emitting portion of the catheter is adjacent to the atheromatous plaque. The light delivery system described in U.S. patent application Ser. No. 5,169,395 (which is hereby incorporated herein by reference) is preferred. The cited patent application describes three constructions for the light emitting portion of the catheter, the selection of which depends on the lesion being treated and/or the diameter of the vessel. For example, if the lesion is located in a large diameter vessel, a balloon catheter preferably is used. The balloon catheter offers the advantage of being introduced low profile (deflated balloon) and then being inflated once in the area of the lesion. Inflating the balloon will serve to displace the light absorbing blood without occluding the vessel. If the photosensitizer used is HPD, total occlusion of the blood may be necessary to minimize attenuation of the therapeutic light by the blood. Again the balloon embodiment would be the catheter of choice. If the lesion is eccentric, the use of the eccentric catheter will allow the device to be more efficiently positioned at the lesion for optimal treatment. Finally, if the treated vessel has a small diameter and approaches the diameter of the remaining non-balloon type catheter, then that catheter would be preferred. In addition to the above, the light dose is about 20-100 J/cm² depending on the thickness of the lesion and the desired amount of light penetration.

However, if smooth muscle cell proliferation is controlled early enough and control maintained until growth factor clears, and if the arterial lumen is sufficiently widened, the light activation therapy may not be necessary, making this solely a pharmacokinetic therapy.

Photosensitizers used in this invention include the following classes: purpurins, verdins, chlorins, phthalocyanines, phorbides, bacterioschlorophylls, porphyrins, chalcogenapyryliums, texaphyrins, xanthenes, benzophenoxazines, phenothiazines, di- and triayl methanes, and kryptocyanines. Preferred members of the above classes are listed in the following table. The optimum light wavelength for activating each member to achieve necrosis is provided in the right column.

seated in the left ostium. Contrast media and x-ray fluoroscopy are used to position all catheters and guidewires during the procedure.

Following a baseline angiogram to reassess the severity of the disease and its location, an atherectomy catheter is advanced to the lesion site through the introducing catheter. A standard atherectomy is performed removing a large portion of the obstruction. The material that was removed from the lesion site can be tested to confirm whether it consists of plaque (cholesterol, calcium, dead foam cells, etc.), intima, and media. If media is present in the explanted material, it can be concluded that the internal elastic lamina was damaged and that smooth muscle cell proliferation will occur unless inhibited by further treatment.

The atherectomy catheter is then removed and the patient is maintained on an anticoagulant (i.e., Heparin) for a period no less than 24 hours after the atherectomy. After this period aspirin is administered every twenty-four hours for a period of two weeks. The photosensitizer (SnET2) also is readministered (at the above described dosage) every twenty-four hours for a period of

TABLE 1

| Class | Preferred Compound | Activation Wavelength (nm) |
| --- | --- | --- |
| Purpurins | Tin Ethyl Etiopurpurin | 600 |
| Verdins | Coproverdin-II-tripotassium Salt | 700 |
| Chlorins | Octaethyl Chlorin | 650 |
| Phthalocyanines | Chloaluminum Sulfonated Phthalocyanine | 665 |
| Phorbides | Mono-L-Aspartyl Chlorin e6 | 660 |
| Bacteriochlorophylls | Bacteriochlorophyll-a | 780 |
| Porthyrins | Protoporphyrin-IX | 630 |
| Chalcogenapyryliums | Chalcogenapyrylium 8b | 800 |
| Texaphyrins | Texaphyrin | 780 |
| Xanthenes | Rhodamine 123 | 480-520 |
| Benzophenoxazines | Nile Blue | 680 |
| Phenothiazines | Methylene Blue | 660 |
| Di- and Triayl Methanes | Victoria Blue-BO | 660 |
| Kryptocyanines | EDKC* | 660-700 |

*EDKC = N,N-bis[2 ethyl-1,3-dioxolane] kryptocyanine

Merely to exemplify a case for the treatment procedure described above, the following may be recited. It is understood that this example is given by way of illustration and not intended to limit the scope of the invention.

Treatment Example

For a patient suffering from a 90% occlusion of the mid-left anterior descending artery wherein the occlusion comprises atheromatous plaque extending a length of 2.0 cm and the vessel has an inner diameter of 2.0 cm, (discovered during a standard angiographic examination) the following treatment is used.

The patient is prepared according to conventional angioplasty procedures. The patient then receives an intravenous injection of Tin Ethyl Etiopurpurin (SnET2) (a photosensitizer) at a dosage in the range of about 0.2-0.6 mg/kg of body weight, and preferably about 0.4 mg per kg of body weight. The carrier used to deliver the SnET2 is lipid emulsion. The concentration of the active ingredient to the carrier is about 0.5-1.5 mg SnET2/ml of carrier.

With an introducing needle, the groin of the patient is pierced until the femoral artery is discovered. Through the introducing needle a guidewire (0.014") is delivered into the femoral artery in a retrograde fashion to the aorta and through the left ostium into the left main artery. The introducing needle is removed and replaced with an introducing catheter. A guiding catheter (i.e., Judkins Left) is introduced over the guidewire and two weeks. The first readministration is carried out 24 hours after the initial administration of the photosensitizer and after the atherectomy. The 24 hour intervals ensure that this particular photosensitizer will maintain the requisite concentration level in the atheromatous tissue and/or plaque, and particularly the smooth muscle cells, necessary to inhibit smooth muscle cell proliferation at the lesion site.

At the end of the two-week photosensitizer readministration period, the patient is seen again at the catheterization laboratory for photodynamic therapy. The patient is prepared according to standard angioplasty procedures. Once the introducing catheter, guidewire, and guide catheter are in place, a light diffusing catheter is advanced over the guidewire to the lesion site. Preferably, the light-diffusing catheter system disclosed in U.S. Pat. No. 5,169,395 is used. The light-diffusing catheter preferably is equipped with radiopaque components to facilitate detecting the position of the catheter with x-ray imaging equipment (or fluoroscopic placement of the catheter).

The wavelength of the light is selected to provide (1) optimal absorption by the photosensitizer and (2) optimal tissue penetration. In this example using SnET2 as the photosensitizer, the selected wavelength of the light is about 660 nanometers. A light dose of 20 Joules/cm² is delivered to the lesion site at a rate of 400 mW/cm² for about 50 seconds as will be described below. The time delay between the last injection and light treatment is about 16–32 hours and optimally 24 hours to permit the photosensitizer to substantially clear normal tissue. After 32 hours, the concentration level of the photosensitizer in the atheromatous cells falls below that necessary for effective cell proliferation inhibition and effective cell lysis.

The light source and light delivery system (light diffusing catheter system) are set up during patient preparation. A light source output is set at 2.0 watts. Then, the light delivery system, having a 1.5 mm diameter and a 2.0 cm diffusing tip, is coupled to the light source with the diffusing tip placed in a power meter designed for reading diffused light, such as an integrating sphere. The power output of the delivery system is then adjusted to 1.0 watt.

When using the 5 Fr. (1.5 mm) catheter with the 2 cm diffusing tip, the catheter diameter creates an annulus of blood flowing around the catheter with a thickness of 0.25 mm. Assuming the lesion is concentric and thin layered, the total surface area of the lesion is 1.256 square cm ($2 \times Pi \times Radius \times Length$). With a light source output of 2.0 watts and a catheter coupling loss of 50% (due to the dead space in the fiber optic bundle), the catheter should have an output of 1.0 watt. Assuming that the blood attenuates 50% of the power in a 0.25 mm thickness, the total power reaching the vessel wall should be 0.5 watts. The power density at the wall will be (0.5 watts/1.256 square cm) 0.4 watts/square cm. With a total delivered dose of 20 Joules/square cm, the total time for the procedure is 50 seconds ((20 Joules/square cm)/(0.4 watts/square cm)).

Following the photodynamic therapy the patient receives anticoagulation medication, such as heparin, for a period no less than twenty-four hours, with aspirin continuing for one week.

The preferred photosensitizing agent is Tin Ethyl Etiopurpurin having the chemical name: Ethyl 3,4,20,21-tetradehydro-4,9,14,19-tetraethyl-18,19-dihydro-3,8,13,18-tetramethyl-20-phorbine carboxylato(2-)-$N^{23}$, $N^{24}$, $N^{25}$, $N^{26}$-tin(IV) dichloride. It has been found that there is little or no retention of this drug in the skin, thereby avoiding problems that can result from exposure of the patient to ordinary sunlight (i.e., activation of the photosensitizer in the skin). In addition, Tin Ethyl Etiopurpurin has a high therapeutic ratio (concentration level in diseased tissue relative to healthy tissue) as compared to other photosensitizers such as hematoporphyrin derivative (HPD). Tin Ethyl Etiopurpurin also is advantageously activated at longer wavelengths (660–690 nanometers). At these wavelengths, the light essentially is not attenuated by the blood as is the case with 630 nanometer wavelength light (the optimum wavelength for HPD, for example). As a result of using a longer activation wavelength, a substantially greater amount of light gets to the vessel wall and photosensitizer, thereby increasing procedure efficiencies. It also is contemplated that the photosensitizer be administered in oral form (e.g., tablet form) to avoid the discomfort and complications of intravenous injection.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A method for treatment of atherosclerosis comprising the steps of:
    administering an effective amount of a photosensitizing agent into a mammal such that the agent accumulates in atherosclerotic smooth muscle cells at a specific location and atherosclerotic plaque adjacent said cells;
    readministering said agent to prevent photosensitizing agent from being substantially cleared from said atherosclerotic smooth muscle cells for a period of at least about 5 days; and
    exposing the photosensitizing agent within said atherosclerotic smooth muscle cells and plaque to light such that said cells and plaque are lysed.

2. The method of claim 1 wherein said photosensitizing agent is Tin Ethyl Etiopurpurin.

3. A method for treatment of atherosclerosis comprising the steps of:
    detecting atherosclerotic smooth muscle cells and plaque in a mammal;
    administering an effective amount of a photosensitizing agent into the mammal such that the agent accumulates in the atherosclerotic smooth muscle cells and plaque;
    widening the lumen of the vessel that has narrowed due to the accumulation of the atherosclerotic smooth muscle cells and plaque; and
    readministering said agent to prevent photosensitizing agent from being substantially cleared from the atherosclerotic smooth muscle cells for a period of at least about five days to essentially prevent growth factor released in the vicinity of said atherosclerotic smooth muscle cells from initiating atherosclerotic smooth muscle cell proliferation.

4. A method for treatment of atherosclerosis comprising the steps of:
    widening the lumen of a vessel that has narrowed due to accumulation of atheromatous plaque; and
    blocking the growth factor binding sites on the atherosclerotic smooth muscle cells injured during the widening step until growth factor is no longer released from the platelets in the vicinity of the injured cells.

5. The method of claim 4 wherein the blocking step is performed continuously for a period of at least about 5 days.

6. The method of claim 5 wherein the blocking step is commenced immediately after the widening step.

7. The method of claim 4 wherein the blocking step is continuous and commenced immediately after the widening step.

8. The method of claim 7 wherein the blocking step is accomplished by introducing an effective amount of a photosensitizing agent in the region of the vessel subject to the widening step such that the agent accumulates in the injured smooth muscle cells.

9. The method of claim 8 wherein the photosensitizing agent is administered such that photosensitizing agent accumulates in the atheromatous plaque.

10. The method of claim 9 further including the step of exposing the photosensitizing agent within the atherosclerotic smooth muscle cells and plaque to light such that said cells and plaque are lysed.

11. The method of claim 8 wherein the photosensitizing agent is a Tin Ethyl Etiopurpurin.

12. The method of claim 8 further including the step of exposing the photosensitizing agent within the atherosclerotic smooth muscle cells to light such that the atherosclerotic smooth muscle cells are lysed.

13. The method of claim 12 wherein the exposing step is commenced after growth factor is no longer released from the platelets in the vicinity of the injured cells.

14. The method of claim 13 wherein the exposing step is commenced within a range of about 5-16 days after the widening step.

* * * * *